United States Patent [19]

Kimura et al.

[11] Patent Number: 5,107,119
[45] Date of Patent: Apr. 21, 1992

[54] METHOD OF EVALUATING CHARACTERISTICS OF SUPERCONDUCTORS AND PROCESS AND APPARATUS FOR FORMING SUPERCONDUCTOR FILM BY USING THE METHOD

[75] Inventors: Takafumi Kimura, Hiratsuka; Hiroshi Nakao, Atsugi; Hideki Yamawaki, Isehara; Masaru Ihara, Chigasaki; Keigo Nagasaka, Nagareyama, all of Japan

[73] Assignee: Fujitsu Limited, Kawasaki, Japan

[21] Appl. No.: 683,421

[22] Filed: Apr. 10, 1991

[30] Foreign Application Priority Data

Apr. 11, 1990 [JP] Japan .................... 2-93925

[51] Int. Cl.⁵ ............................ G01J 21/35
[52] U.S. Cl. .................... 250/341; 250/336.2; 505/842; 427/62
[58] Field of Search ........ 250/341, 336.2; 427/62, 427/63; 505/842, 843, 847

[56] References Cited

U.S. PATENT DOCUMENTS 4,490,612 12/1984 Törmälä250 .................. 341/
4,837,438 6/1989 Strum ........................... 250/341
4,845,730 7/1989 Marer .......................... 250/341
4,937,449 6/1990 Kreuzer et al. ................. 250/341

OTHER PUBLICATIONS

"Derivation of an Expression for the Conductivity of Superconductors in Terms of the Normal-State Conductivity", Luc Leplae, Physical Review B, vol. 27, No. 3, Feb. 1, 1983, pp. 1911–1912.

Primary Examiner—Carolyn E. Fields
Assistant Examiner—Drew A. Dunn
Attorney, Agent, or Firm—Armstrong, Nikaido, Marmelstein, Kubovcik & Murray

[57] ABSTRACT

A method of evaluating the characteristics of superconductors, comprising: irradiating light to a superconductor held at a predetermined temperature; detecting light transmitted through the superconductor and composing a spectrum of the transmitted light; and using the obtained spectrum, calculating a ratio of the number of electrons contributing to a normal conduction to the number of electrons contributing to a superconduction in the superconductor, the ratio being effective at said predetermined temperature. A process and an apparatus for forming superconductor films by using the method are also disclosed.

12 Claims, 9 Drawing Sheets

METHOD OF EVALUATING CHARACTERISTICS OF SUPERCONDUCTORS AND PROCESS AND APPARATUS FOR FORMING SUPERCONDUCTOR FILM BY USING THE METHOD

BACKGROUND OF THE INVENTION

1. Field of the Invention

The present invention relates to a method of evaluating the characteristics of superconductors, a process for forming a superconductor film by using the method, and an apparatus for carrying out the process.

2. Description of the Related Art

The recent research into and development of high temperature superconductors has included an application thereof to electronic elements such as semiconductor devices.

The mechanism of this superconduction is not absolutely clear, however, and a method of evaluating the characteristics of superconductors has not been established. Particularly, in the case of a superconductor film formed by a chemical vapor deposition (CVD), a molecular beam epitaxy (MBE), sputtering, vapor deposition, or the like, the mass to be evaluated is so small that the available evaluation methods are limited in that an evaluation at a required precision is impossible, and this has raised a problem in the developing of a superconductor film having a good crystalline structure and applicable to electronic elements.

Namely, in the conventional evaluation method, the ratio of the number of electrons contributing to a normal conduction to the number of electrons contributing to a superconduction in a superconductor is evaluated by measuring the magnetic susceptibility of the superconductor. The magnetic susceptibility can be measured at a high precision when the mass to be measured has a large volume, such as a bulk material produced by a sintering process or the like, but when the mass to be measured has a minute volume such as a film material, a required sensitivity cannot be obtained and the characteristics of a superconductor cannot be precisely evaluated.

Because the superconductive property of a superconductor depends greatly not only upon the chemical composition thereof but also upon the process conditions during the forming thereof such as the forming temperature, it is necessary to evaluate the characteristics of a superconductor during the growth thereof and to feed back the evaluated results to the process conditions to thereby form a superconductor having a good characteristic. The conventional process and apparatus for forming a superconductor film, however, does not provide a method of evaluating the characteristics of a film during the forming thereof, and thus an effective feedback is not possible.

SUMMARY OF THE INVENTION

The object of the present invention is to provide a method of evaluating the characteristic of superconductors at a high precision even when the mass to be evaluated is small, a process for forming a superconductor film by using this evaluation method to evaluate the characteristic of a film during the forming thereof and control the process conditions based on the result of the evaluation, and an apparatus for carrying out this process.

To achieve the object according to the present invention, there is provided a method of evaluating the characteristics of superconductors, comprising:

irradiating light to a superconductor held at a predetermined temperature;

detecting light transmitted through the superconductor and composing a spectrum of the transmitted light; and using the spectrum to calculate a ratio of the number of electrons contributing to a normal conduction to the number of electrons contributing to a superconduction in the superconductor, the ratio being effective at said predetermined temperature.

The method according to the present invention measures the spectrum of light transmitted through a superconductor and evaluates, from variations of the light transmitted or transmittance, the ratio of the number of electrons contributing to a normal conduction (hereinafter referred to as "normal conduction electrons") to the number of electrons contributing to a superconduction (hereinafter referred to as "superconduction electrons").

The irradiation is conveniently effected with an infrared or extreme infrared ray. The measurement of these rays has been well established and is conventionally carried out to provide a precise evaluation of the characteristics of metal or semiconductor films, and therefore, is readily applicable to the evaluation of a minute quantity such as a superconductor film.

The calculation according to the present invention preferably comprises:

comparing an observed spectrum of the transmitted light with a theoretical spectrum defined by the following formula (1); and calculating the ratio by using the following formula (2).

$$T = \frac{(1-R)^2 \left(1 + \frac{K^2}{n^2}\right) e^{-\alpha d}}{(1 - Re^{-\alpha d})^2 + 4Re^{-\alpha d}\sin^2(\phi - \theta)} \quad (1)$$

provided $$R = \frac{(n-1)^2 + K^2}{(n+1)^2 + K^2}, \alpha = \frac{\omega}{cn}\epsilon_2$$

$$n = (((\epsilon_1^2 + \epsilon_2^2)^{\frac{1}{2}} + \epsilon_1)/2)^{\frac{1}{2}},$$

$$k = (((\epsilon_1^2 + \epsilon_2^2)^{\frac{1}{2}} - \epsilon_1)/2)^{\frac{1}{2}},$$

$$\theta = knd,$$

$$\tan \phi = \frac{-2k}{n^2 + k^2 - 1}$$

where R: reflectance, n: real part of complex refractive index, k: imaginary part of complex refractive index, $\alpha$: absorption coefficient, d: thickness of sample.

$$\epsilon = \epsilon^\infty + f_n\epsilon_d + (1-f_n)\epsilon_s \quad (2)$$

where $\epsilon$: complex dielectric constant, $\epsilon^\infty$: high frequency term not contributing to conduction, $\epsilon_d$: term due to normal conduction electrons (or free electron gas), which conforms to Drude's formula and is defined as;

$\epsilon_d = \epsilon_{1d} - i\epsilon_{2d}.$ provided $$\epsilon_{1d} = -\frac{\omega_p^2 \tau^2}{\omega^2 \tau^2 + 1},$$

$$\epsilon_{1d} = -\frac{\omega_p^2 (\tau/\omega)}{\omega^2 \tau^2 + 1},$$

$$\epsilon_p^2 = \frac{N e^2}{\epsilon_0 m^*}$$

where $\tau$: relaxation time of carrier
$\omega_p$: plasma frequency
N: electron density
$m^*$: effective mass of electron
$\epsilon_s$: term due to superconduction electrons and defined as;

$\epsilon_s = \epsilon_{1s} - i\epsilon_{2s}$ where $\epsilon_0 \epsilon_{2s} = \sigma_{1s}/\omega$ and $\epsilon_0 \epsilon_{1s} = -\sigma_{2s}/\omega$, $\sigma_{1s}$ and $\sigma_{2s}$ being the real part and the imaginary part of the optical conductivity spectrum of a superconductor and conforming to Mattis-Bardeen's rule, and $f_n$: ratio of the number of normal conduction electrons to the total numbers of electrons contributing to conduction.

The real part $\sigma_{1s}$ and the imaginary part $\sigma_{2s}$ which conform to Mattis-Bardeen's rule are expressed as follows:

$$\sigma_{1s}/\sigma_n = \frac{2}{\hbar\omega} \int_{\Delta}^{\infty} [f(E) - f(E + \hbar\omega)] g(E) dE +$$

$$\frac{1}{\hbar\omega} \int_{\Delta - \hbar\omega}^{-\Delta} [1 - f(1 - \hbar\omega)] g(E) dE$$

$$\sigma_{2s}/\sigma_n =$$

$$\frac{1}{\hbar\omega} \int_{\Delta - \hbar\omega, -\Delta}^{\Delta} \frac{[1 - 2f(E + \hbar\omega)][E^2 + \Delta^2 + \hbar\omega E]}{[\Delta^2 - E^2]^{\frac{1}{2}}[(E + \hbar\omega)^2 - \Delta^2]^{\frac{1}{2}}} dE$$

where $f(\eta) = \frac{1}{1 + e^{\eta/kT}}$; Fermi function, $g(E) = \frac{[E^2 + \Delta^2 + \hbar\omega E]}{[E^2 - \Delta^2]^{\frac{1}{2}}[(E + \hbar\omega)^2 - \Delta^2]^{\frac{1}{2}}}$, and $\sigma_n$: electric conductivity under normal conduction.

The following formula (1A) expresses the transmission spectrum T at a higher precision than formula (1).

$$T = T_{0,j} = t_{0,j} t_{0,j}^* \tag{1A}$$

wherein, $$r_{0,j} = r_{0,j-1} + \frac{t_{0,j-1} \cdot t_{j-1,0} e^{-2i\Delta_j}}{1 + r_{j-1,0} \cdot r_{j-1,j} e^{-2i\Delta_j}}$$

-continued $$t_{0,j} = \frac{t_{0,j-1} \cdot t_{j-1,j} e^{-i\Delta_j}}{1 - r_{j-1,0} \cdot r_{j-1,j} e^{-2i\Delta_j}}$$

where $r_{k,l}$ represents the phase and amplitude of light once reflected through the k-th to the l-th layers in a multiple-layered film composed of j layers, $t_{k,l}$ represents the phase and amplitude of light once transmitted through the k-th to the l-th layers in a multiple-layered film composed of j layers, and $e^{-i\Delta_n}$ represents the phase shift and damping in the material of the n-th layer, in which $\Delta_n = (d_n/\lambda)/2\pi + ie^{-\alpha_n d_n}$, $d_n$ being the thickness of the n-th layer and $\alpha_n$ being the damping of the n-th layer.

The real part $\sigma_{1S}$ and the imaginary part $\sigma_{2S}$ of the optical conductivity spectrum of a superconductor may preferably conform to Leplae's theory, as defined by the following formule:

$$\sigma_{1d}(\omega, V_F\tau) =$$

$$\frac{1}{2\hbar\omega} \int_{\Delta}^{\hbar\omega - \Delta} \{[g(E) + 1]\sigma_{1d}(|\epsilon'| + |\epsilon|, V_F\tau) +$$

$$[g(E) - 1]\sigma_{1d}(|\epsilon'| - |\epsilon|, V_F\tau)\} dE$$

$$\sigma_{2d}(\omega, V_F\tau) = \frac{2A(V_F\tau)}{\pi\omega} + \frac{2\omega}{\pi} \int_{0+}^{\infty} \frac{\sigma_{1d}(\omega', V_F\tau)}{\omega^2 - \omega'^2} d\omega'$$

with $\epsilon, \epsilon'$: energy of a single particle electron measured from Fermi surface, $\epsilon'$ being the energy under an excited state, $g$ (E): $(EE' - \Delta^2)/|\epsilon\epsilon'|$, $\Delta$: energy gap, $\sigma_{1d}$: $\sigma_0/(1 + \omega^2\tau^2)$ [derived from Drude's equation], $$A(V_F\tau) = \int_0^{\infty} \sigma_{1d}(\omega, V_F\tau) d\omega - \int_0^{\infty} \sigma_{1s}(\omega, V_F\tau) d\omega$$

$\sigma_0$: direct current electric conductivity, and
$V_F$: Fermi velocity.

There is also provided, according to the present invention, a process for forming a superconductor film on a substrate, comprising:

using the evaluation method of the present invention to evaluate characteristics of a superconductor during the growth thereof on a substrate; and controlling a process condition based on the evaluation.

The present inventive process for forming a superconductor film ensures that the characteristics of a superconductor film are evaluated at any time during the growth thereof and the results of the evaluation are fed back to adjust the process conditions and thus control the growth of the film to an optimum condition providing the formed film with a good crystalline structure.

The forming of the superconductor film on the substrate may be carried out by a usual process for forming a film on a substrate, such as a chemical vapor deposition (CVD), a molecular beam epitaxy (MBE), a sputtering, or a vapor deposition.

According to the present invention, there is also provided an apparatus for forming a superconductor film on a substrate, comprising:

a growth chamber in which a superconductor film is formed on a substrate;

a means for measuring a light transmittance of a superconductor film on the substrate; and a mechanism for transferring the substrate and the film between the growth chamber and the means for measuring a light transmittance.

The means for measuring a light transmittance of a superconductor film preferably comprises: a portion for generating light; a portion for detecting light; a light pipe for communicating the light generating portion with the light detecting portion; and a means, inserted in the light pipe, for supporting the substrate with the film at the path of light passing through the light pipe; wherein the mechanism for transferring the substrate and the film is able to transfer the substrate and the film between the growth chamber and the substrate supporting portion of the means for measuring a light transmittance of the film.

Preferably, an intermediate space is provided between the growth chamber and the substrate supporting means, for a temporary containing of the substrate and the film when moving between the growth chamber and the substrate supporting means.

The present inventive apparatus preferably further comprises a temperature regulator and a pressure regulator for maintaining a temperature and a pressure in the intermediate space at a value between those of the growth chamber and those of the substrate supporting means.

The present inventive apparatus for carrying out the present inventive process may be arranged by incorporating a device for measuring the light transmittance in a conventional apparatus for forming a film on a substrate, such as a chemical vapor deposition apparatus, a molecular beam epitaxy apparatus, a sputtering apparatus, a vapor deposition apparatus, or the like.

DESCRIPTION OF THE PREFERRED EMBODIMENTS

Figure 1:
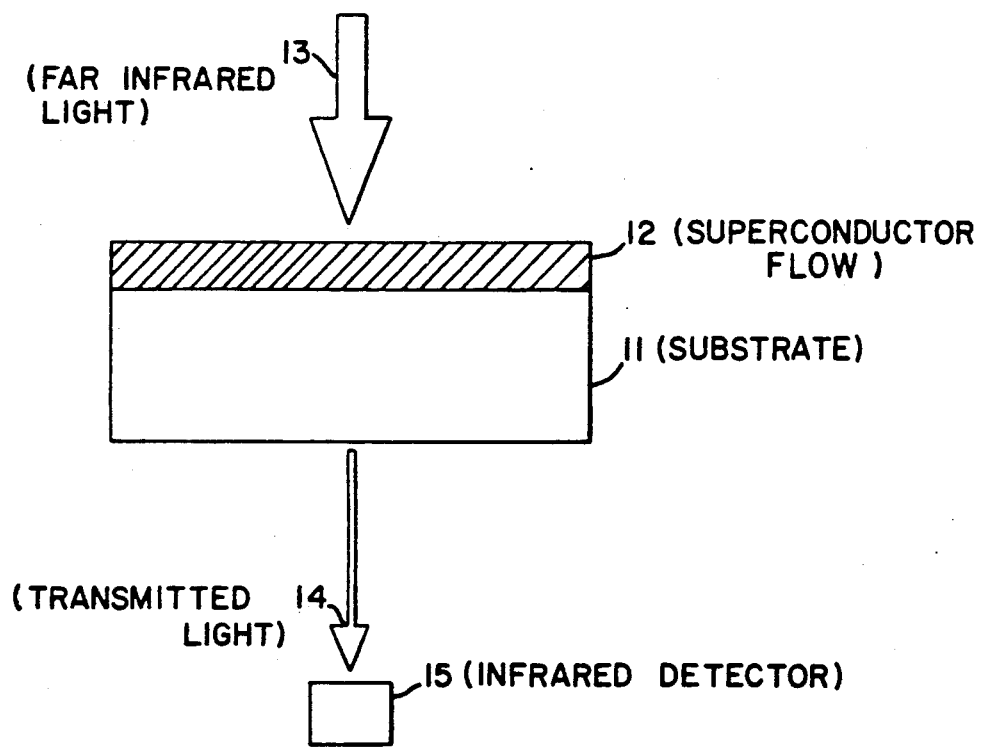
FIG. 1 schematically illustrates a measurement of the transmittance of a superconductor film formed on a substrate.

The principle of the present invention will be described below.

The ratio of the number of normal conduction electrons to that of superconduction electrons (hereinafter referred to as "the normal/superconduction electron number ratio") is obtained on the following basis.

Substances have a specific wave length of light which can be easily absorbed by or transmitted through the substance and the characteristics of the substance can be determined by the measurement of such wave lengths. The present inventors found that, by utilizing this phenomenon, the normal/superconduction electron number ratio of superconductors having a complicated crystalline structure can be determined.

The optical conductivity spectrum of substances has been studied and clarified for the conventional normal conductors or superconductors, but the recently found and developed oxide superconductors have a complicated crystalline structure and consist essentially of a mixed crystal, in which the normal conduction electrons and the superconduction electrons coexist and both the normal conduction and superconduction electrons must be collectively taken into consideration when determining the optical conductivity spectrum.

The optical conductivity spectrum, $\sigma$, has a relationship with the complex dielectric constant $\epsilon$, as expressed by the formula:

$$\sigma = \omega \epsilon_0 \epsilon,$$

where $\omega$ is the frequency of light and $\epsilon_0$ is the dielectric constant of vacuum.

Assuming a sample is a mixed crystal of a normal conductor and a superconductor, the complex dielectric constant $\epsilon$ of the sample can be expressed as:

$$\epsilon = \epsilon^\infty = f_n \epsilon_d + (1 - f_n) \epsilon_s \tag{2}$$

where $\epsilon$: complex dielectric constant, $\epsilon^\infty$: high frequency term not contributing to conduction, $\epsilon_d$: term due to normal conduction electrons (or free electron gas), which conforms to Drude's formula and defined as;

$$\epsilon_d = \epsilon_{1d} - i\epsilon_{2d},$$

provided $$\epsilon_{1d} = -\frac{\omega_p^2 \tau^2}{\omega^2 \tau^2 + 1},$$

$$\epsilon_{1d} = -\frac{\omega_p^2 (\tau/\omega)}{\omega^2 \tau^2 + 1},$$

$$\epsilon_p^2 = \frac{Ne^2}{\epsilon_0 m^*}$$

where $\tau$: relaxation time of carrier
$\omega_p$: plasma frequency
N: electron density
$m^*$: effective mass of electron
$\epsilon_s$: term due to superconduction electrons and defined as:

$$\epsilon_s = \epsilon_{1s} - i\epsilon_{2s}$$

where
$\epsilon_0 \epsilon_{2s} = \sigma_{1s}/\omega$ and $\epsilon_0 \epsilon_{1s} = -\sigma_{2s}/\omega$, $\sigma_{1s}$ and $\sigma_{2s}$ being the real part and the imaginary part of the optical conductivity spectrum of a superconductor which conforms to Mattis-Bardeen's rule [see D. C. Mattis and J. Bardeen, "Theory of Anomalous Skin Effect in Normal and Superconducting Metals", Phys. Rev. Vol. 111, pp. 412–417, 15 July 1985], and $f_n$: ratio of the number of normal conduction electrons to the total numbers of electrons contributing to conduction.

Consequently, the transmission spectrum T is expressed as:

$$T = \frac{(1-R)^2 \left(1 + \frac{K^2}{n^2}\right) e^{-\alpha d}}{(1 - Re^{-\alpha d})^2 + 4Re^{-\alpha d}\sin^2(\phi - \theta)} \quad (1)$$

provided $$R = \frac{(n-1)^2 + K^2}{(n+1)^2 + K^2}, \quad \alpha = \frac{\omega}{cn}\epsilon^2$$

$$n = (((\epsilon_1^2 + \epsilon_2^2)^{\frac{1}{2}} + \epsilon_1)/2)^{\frac{1}{2}},$$

$$k = (((\epsilon_1^2 + \epsilon_2^2)^{\frac{1}{2}} - \epsilon_1)/2)^{\frac{1}{2}},$$

$$\theta = knd,$$

$$\tan\phi = \frac{-2k}{n^2 + k^2 - 1}$$

where R: reflectance, n: real part of complex refractive index, k: imaginary part of complex refractive index, $\alpha$: absorption coefficient, d: thickness of sample.

The optical conductivity spectrum has been studied as a physical quantity expressing the material nature, but in the experimental field, information about the transmission spectrum best expresses the material property. This is the reason for using the transmission spectrum derived from the optical conductivity spectrum, instead of the latter.

By using $f_n$ as a parameter and matching an experimental transmission spectrum with the theoretical spectrum, the normal/superconduction electron number ratio can be obtained. Preferably, the normal/superconduction electron number ratio is obtained from the infrared or far-infrared transmission spectrum.

The present invention will be described in more detail by way of Examples.

EXAMPLE 1

The normal/superconduction electron number ratio of an oxide superconductor film is estimated in the following sequence, according to the present invention.

FIG. 1 schematically illustrates the principle of the measurement of an infrared transmission spectrum. The transmission spectrum of a superconductor film 12 formed on a substrate 11 is obtained by irradiating an infrared or far-infrared ray 13 to the film 12, and measuring the transmitted light 14 by an infrared or far-infrared ray detector 15. The normal/superconduction electron number ratio of the superconductor 12 is derived from the thus-obtained transmission spectrum.

Figure 2:
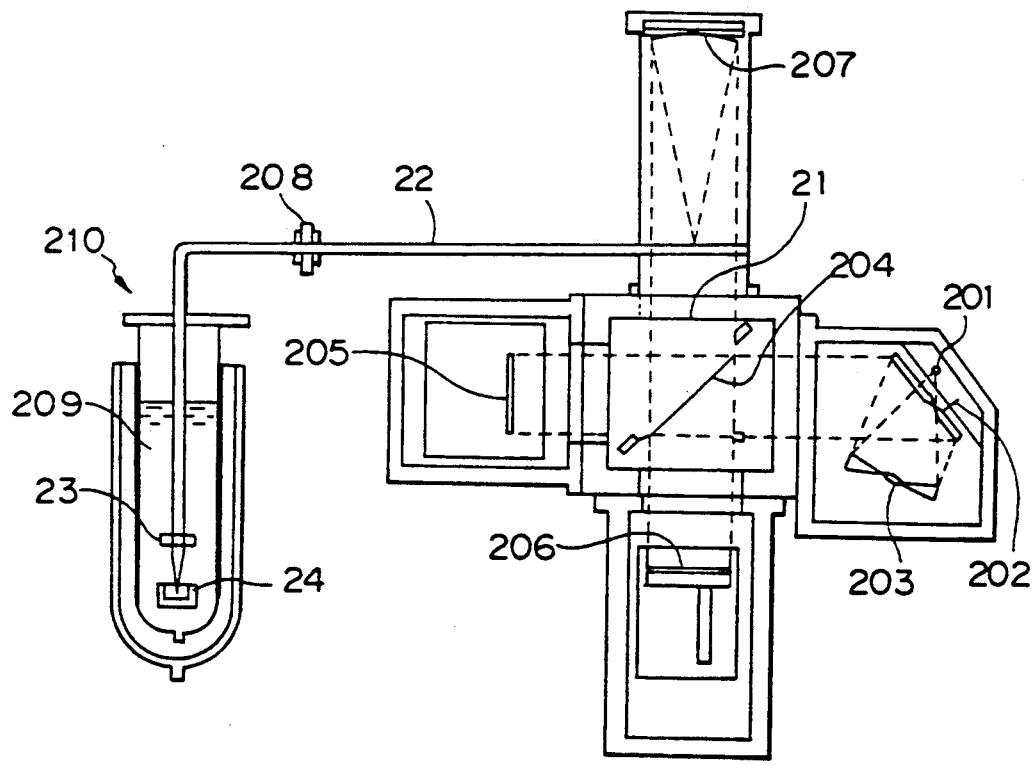
FIG. 2 shows a typical arrangement of Michelson interferometer.

FIG. 2 shows a Michelson interferometer used for measuring the transmission spectrum. An infrared or far-infrared ray introduced through an optical window 21 is irradiated to a sample 23 via a light pipe 22, and the infrared or far-infrared ray transmitted through the sample 23 is detected by a detector 24 such as a bolometer. In the figure, 201 denotes a light source, 202 a chopper, 203 a collimator, 204 a beam splitter, 205 a stationary mirror, 206 a movable mirror, 207 a focus mirror, 208 a filter, 209 a coolant such as liquid nitrogen or liquid helium, and 210 a cryostat.

The above-observed values are analyzed by comparing same with the theoretically calculated values, to provide the normal/superconduction electron number ratio.

Figure 3A:
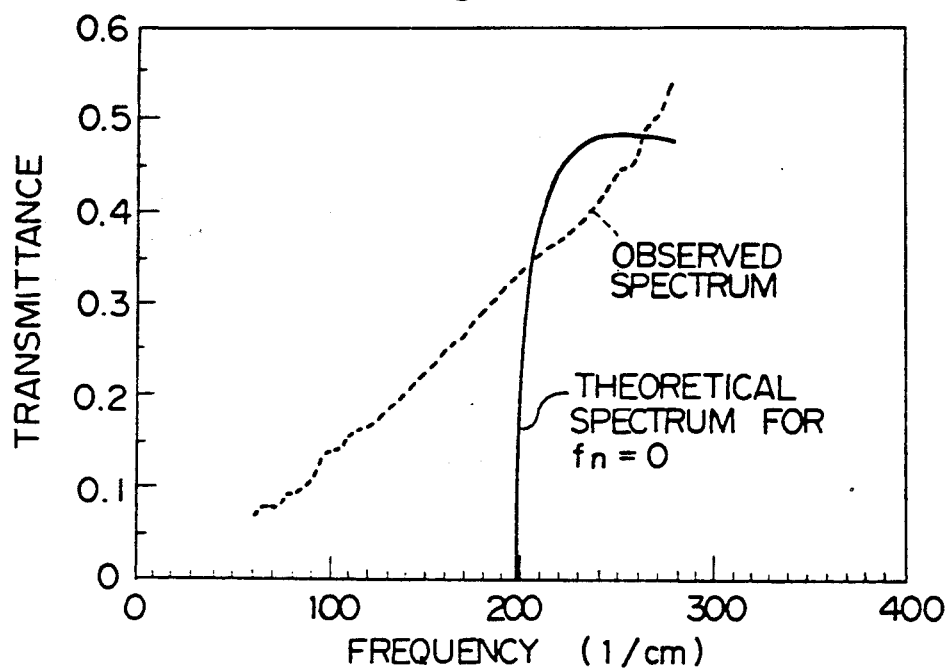
FIGS. 3 (a), (b), and (c) are graphs showing (a) an observed experimental transmission spectrum in comparison with a theoretical transmission spectrum of a superconductor not containing normal conduction electrons ($f_n = 0$), (b) these spectrums matched by using $f_n$ as a parameter according to the present invention, and (c) the theoretical transmission spectra corresponding to different values of the number of normal conduction electrons or fitting parameter $f_n$.
Figure 3B:
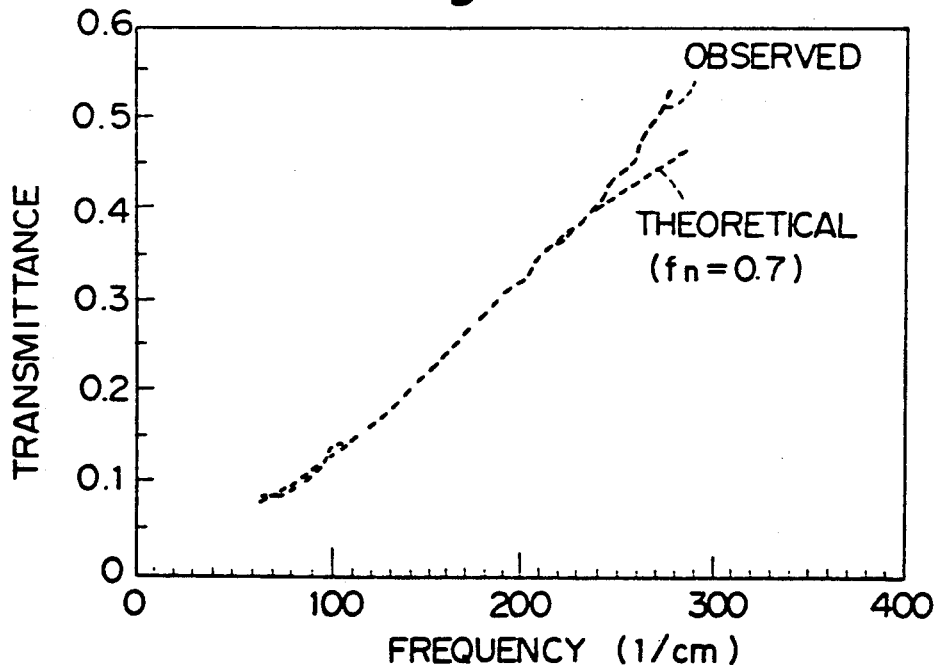
Figure 3C:
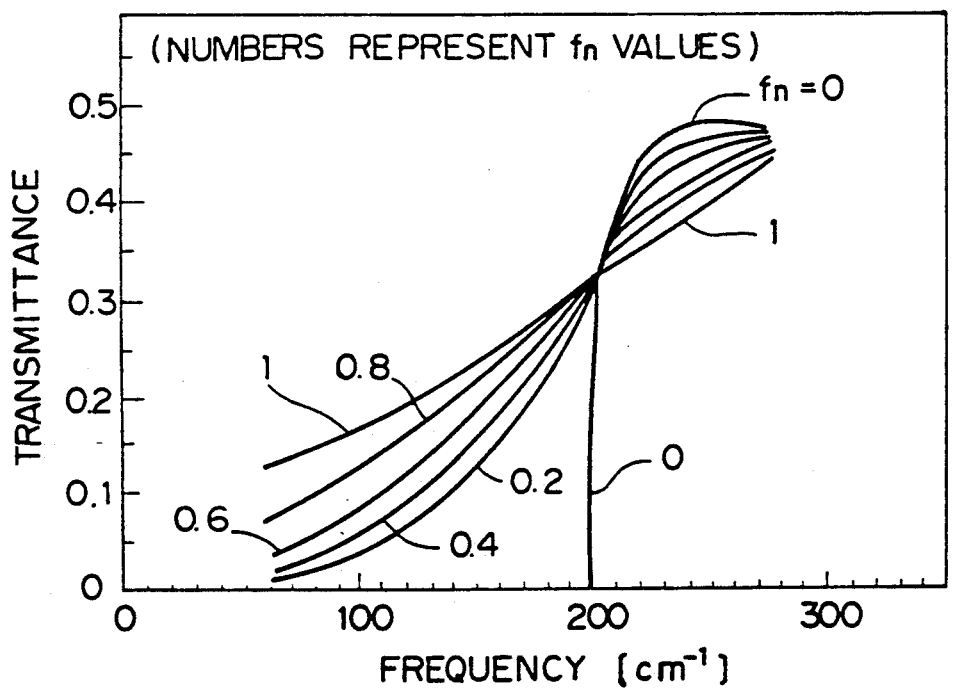

FIG. 3 (a) shows a transmission spectrum obtained by a measurement of an approximately 150 nm thick Bi-superconductor film formed on an approximately 0.4 mm thick MgO substrate by a chemical vapor deposition (CVD) process. The measurement was carried out over a range of the light frequency of from 50 to 300 cm$^{-1}$, and the observed transmittance varies continuously with respect to the frequency, as shown by the broken curve. The solid curve represents the theoretical transmission spectrum for an ideal or pure superconductor. This result shows that the actual sample (23) is a mixed crystal of a normal conductor and a superconductor.

FIG. 3 (b) shows a comparison between the above-observed spectrum and the theoretical spectrum for a normal/superconduction electron number ratio $f_n = 0.7$, in which both spectrums match very well to thus prove that the sample has a normal/superconduction electron number ratio of 0.7 to 0.8.

The theoretical spectrum varies with the matching parameter $f_n$ as shown in FIG. 3 (c). The $f_n$ value at which the observed and the theoretical spectra best match is the ratio of the normal/superconduction electron number ratio of the sample subjected to the measurement.

As described above, the present inventive evaluation method enables the normal/superconduction electron number ratio of superconductors to be easily obtained.

EXAMPLE 2

Figure 4:
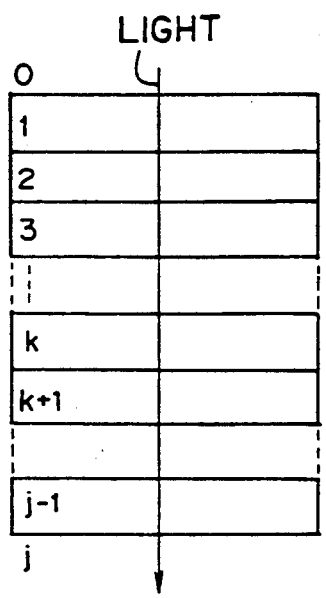
FIG. 4 schematically illustrates a light-transmitting material having a multiple-layered structure.

For a material having a multi-layer structure as shown in FIG. 4, the transmission spectrum T of light is calculated in the following manner.

Figure 5:
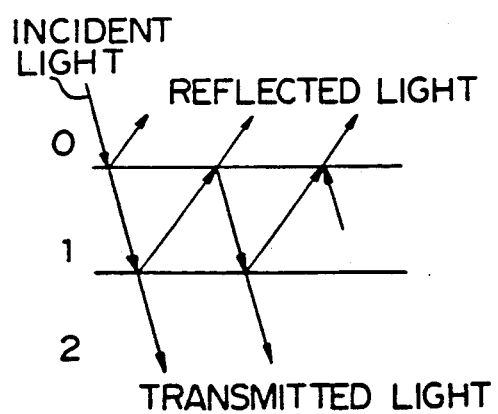
FIG. 5 schematically illustrates reflection and transmission of light through two layers.

Considering a multiple reflection by two layers as shown in FIG. 5, the reflected light and the transmitted light are expressed, respectively, as:

$$r_{0,2} = r_{0,1} + t_{0,1} \cdot t_{1,0} \cdot r_{1,2} e^{-i\Delta_1} \sum_{n=0}^{\infty}(r_{1,0}\, r_{1,2}\, e^{-2i\Delta_1})^n$$

$$= r_{0,1} + (t_{0,1} \cdot t_{1,0}\, e^{-2i\Delta_1})/(1 + r_{1,0}\, r_{1,2}\, e^{-2i\Delta_1})$$

$$t_{0,2} = t_{0,1}\, t_{1,2} \sum_{n=0}^{\infty}(r_{1,2}\, r_{1,0}\, e^{-2i\Delta_1})^n$$

$$= (t_{0,1}\, t_{1,2}\, e^{-i\Delta_1})/(1 - r_{1,0}\, r_{1,2}\, e^{-2i\Delta_1})$$

with $r_{k,l}$: light once reflected when the k-th through the l-th layers are supposed to be monolithic, $t_{k,l}$: light once transmitted when the k-th through the l-th layers are supposed to be monolithic, $e^{-i\Delta_n}$: phase shift and damping in the n-th layer, $\Delta_n = (d_n/\lambda)2\pi + ie^{-\alpha_n d_n}$, $d_n$ being the thickness of the n-th layer and $\alpha_n$ being the damping factor of the n-th layer.

Thus, the reflected light and the transmitted light for a film composed of j layers of FIG. 4 can be expressed as:

$$r_{0,j} = r_{0,j-1} + (t_{0,j-1} \cdot t_{j-1,0} e^{-2i\Delta_j})/(1 + r_{j-1,0} r_{j-1,j} e^{-2i\Delta_j})$$

$$t_{0,j} = (t_{0,j-1} t_{j-1,j} e^{-i\Delta_j})/(1 - r_{j-1,0} r_{j-1,j} e^{-2i\Delta_j})$$

By using the above-equations, the reflected light and the transmitted light for a structure composed of j layers can be calculated by a layer-by-layer calculation from the first layer to the j-th layer, to provide expressions for the transmission spectrum T and the reflection spectrum R as follows:

$$T = T_{0,j} = t_{0,j} t_{0,j}^*$$

$$R_{0,j} = r_{0,j} r_{0,j}^*$$

Using this theoretical spectrum T, the transmission spectrum T can be calculated for the same sample as used in Example 1.

The sample of Example 1 has a structure of BSCCO/MgO, in which $j=3$, i.e.;

0, 3: vacuum,
1: Bi—Sr—Ca—Cu—O superconductor film, and
2: MgO-substrate.

T is expressed as:

$$T = (T_{0,2} T_{2,3} e^{-\alpha d})/(1 - R_{2,0} R_{2,3} e^{-2\alpha d})$$

Figure 6:
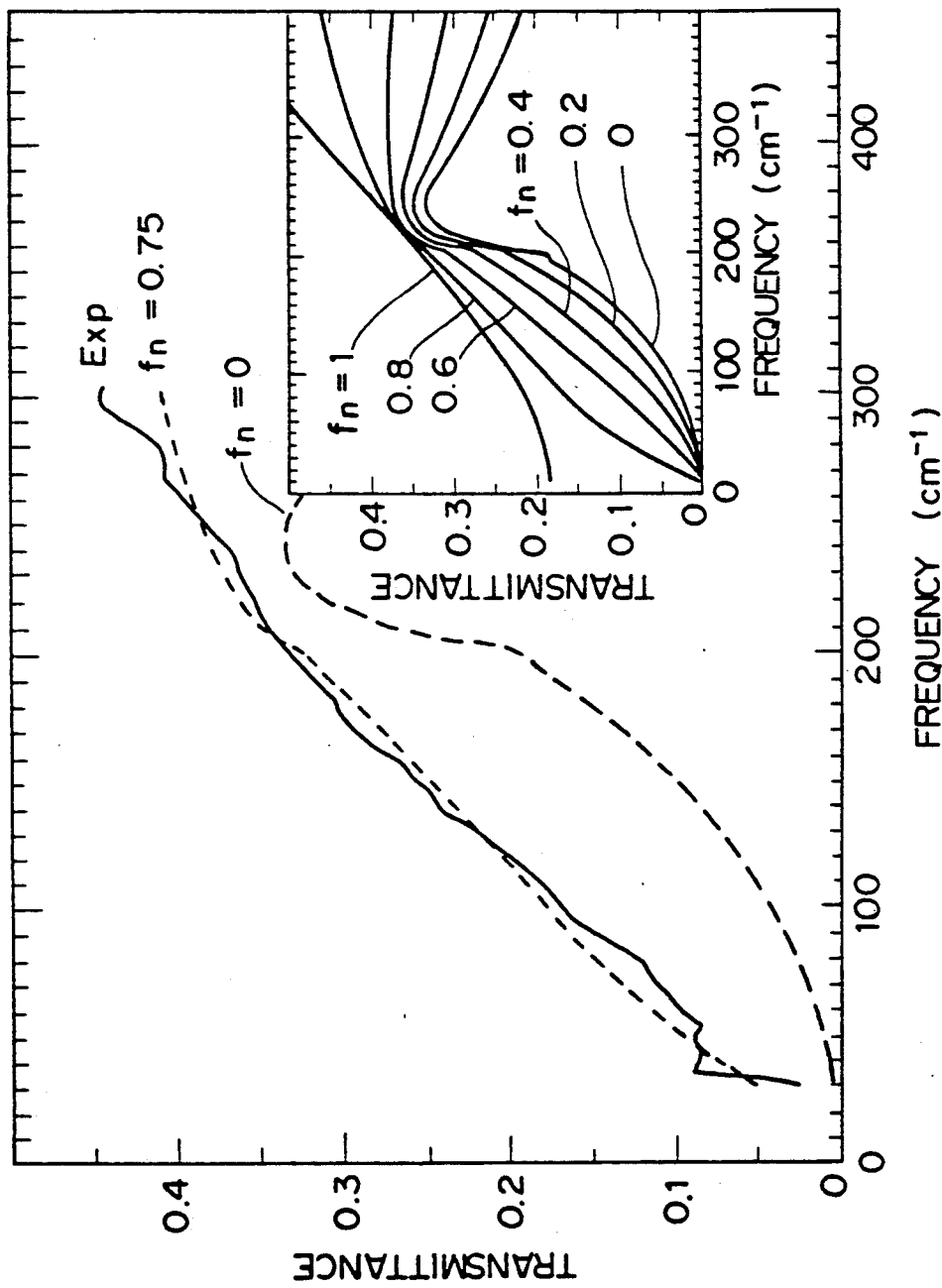
FIG. 6 is a graph showing a matching of the theoretical and the experimental transmission spectra to yield a $f_n$ of 0.75, according to a preferred embodiment of the present invention.

Using this expression, the transmission spectrum T is obtained in the same sequence as in Example 1, as shown in FIG. 6. The result shows that the normal/superconduction electron number ratio $f_n = 0.75$.

In Example 1, the calculation was carried out without considering the presence of the MgO substrate. In Example 2, the calculation involves the effect of the MgO substrate and provides a more precise evaluation of $f_n$. When a sample has a high $f_n$ value, the calculations of both Example 1 and Example 2 give substantially the same $f_n$ value as seen from FIG. 6 and FIG. 3(c). Therefore, when the $f_n$ is expected to have a high value, the simpler calculation as used in Example 1 is preferable.

This embodiment also provides an evaluation of a multi-layer film composed of superconductive, normal conductive, and insulating layers.

EXAMPLE 3

In Example 1, the transmission spectrum T was calculated on the assumption that the optical conductivity spectrum conforms to Mattis-Bardeen's rule. Mattis-Bardeen's theory is best applied in those cases in which a wave number $\omega_g$ corresponding to the energy gap $\Delta$ is smaller than the inverse number of the life time $\tau$ of quasiparticles ($\omega_g << 1/\tau$), as in the metallic superconductors. In Example 1, the transmission spectrum T was calculated by using this theory.

The embodiment of Example 3 provides a more precise evaluation of the transmission spectrum T.

Considering a relatively higher $\omega_g$ value of the Bi containing or the copper oxide containing superconductors ($\omega_g >> 1/\tau$), it is more advantageous to use an optical conductivity spectrum conforming to Leplae's theory instead of Mattis-Bardeen's rule, as described below.

According to Leplae's theory (see L. Leplae, Phys. Rev. Vol. B27 (1983), p. 1911), the real part $\sigma_{1s}$ and the imaginary part $\sigma_{2s}$ of the optical conductivity spectrum T can be expressed as:

$$\sigma_{1s}(\omega, V_F \tau) = \frac{1}{2\hbar\omega} \int_\Delta^{\hbar\omega - \Delta} \{[g(E) + 1]\sigma_{1d}(|\epsilon'| + |\epsilon|, V_F \tau) + [g(E) - 1]\sigma_{1d}(|\epsilon'| - |\epsilon|, V_F \tau)\} dE$$

where $\epsilon, \epsilon'$: energy of a single particle electron measured from Fermi surface, $\epsilon'$ being the energy under an excited state, $g$ (E): $(EE' - \Delta^2)/|\epsilon \epsilon'|$, $\Delta$: energy gap, $\sigma_{1d}$: $\sigma_0/(1 + \omega^2 \tau^2)$ [derived from Drude's equation], $\sigma_0$: direct current electric conductivity, and $V_F$: Fermi velocity.

$$\sigma_{2s}(\omega, V_F \tau) = \frac{2A(V_F \tau)}{\pi \omega} + \frac{2\omega}{\pi} \int_{0+}^{\infty} \frac{\sigma_{1s}(\omega', V_F \tau)}{\omega^2 - \omega'^2} d\omega'$$

where $$A(V_F \tau) = \int_0^\infty \sigma_{1d}(\omega, V_F \tau) d\omega - \int_0^\infty \sigma_{1s}(\omega, V_F \tau) d\omega$$

Figure 7:
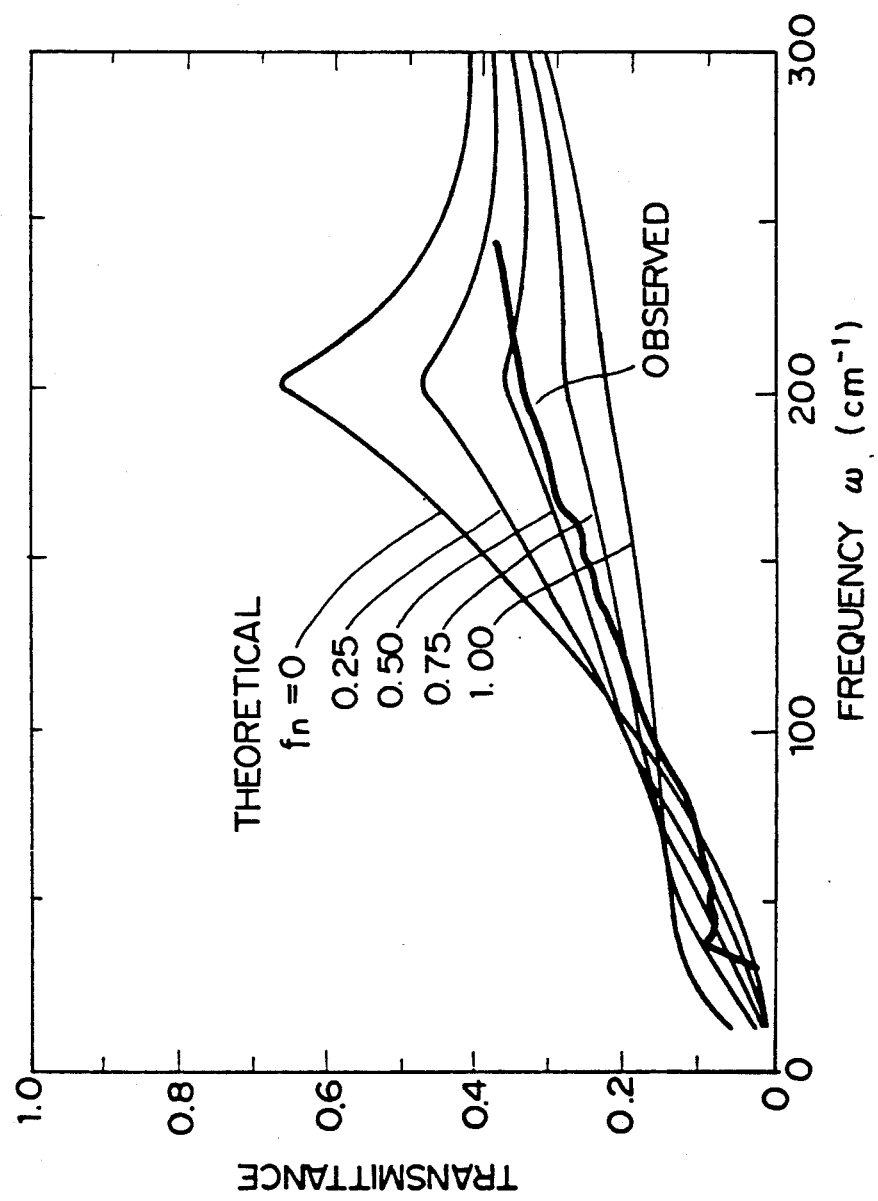
FIG. 7 is a graph showing another matching of the theoretical and the experimental transmission spectra to yield an $f_n$ of 0.6–0.7, according a more preferred embodiment of the present invention.

By using these $\sigma_{1s}$ and $\sigma_{2s}$ and incorporating the above-mentioned multiple-layer effect, the transmission spectrum T is calculated in the same sequence to yield the result as shown in FIG. 7, in which $\omega_p = 800$ cm$^{-1}$, $\tau = 2 \times 10^{-14}$ sec, $\omega_g = 200$ cm$^{-1}$, and $d = 0.05$ $\mu$m. A comparison of this calculated T with the experimental T shows that $f_n = 0.6$–$0.7$.

This embodiment of the present invention provides a more precise evaluation of the transmission spectrum T by using Leplae's theory, in which the relationship between the energy gap $\Delta$ and the quasiparticle life time $\tau$ is taken into consideration.

EXAMPLE 4

An apparatus for forming a superconductor film by using the present invention evaluation method will be described below.

FIG. 7 shows an arrangement of an apparatus for forming superconductor films, such as a CVD apparatus, a vapor deposition apparatus, a sputtering apparatus, an MBE apparatus, or the like, and which incorporates a device for measuring the transmittance similar to the device used in Example 1.

A superconductor film 12 (FIG. 1) formed on a substrate 11 (FIG. 1) in a growth chamber 3 can be transferred between the growth chamber 3 and a film supporting portion 4 by a transfer mechanism 2. The provision of the transfer mechanism 2 enables the superconductor film growing on the substrate to be taken out of the growth chamber 3 at any time during the growth for a measurement of the infrared or far-infrared transmission spectrum. After the measurement, the film can be returned to the growth chamber 3, to effect the subsequent growth. The inside of a film supporting portion 4 of the infrared or far-infrared spectrometer is evacuated by a vacuum pump 7 and maintained at a vacuum, and a cooler 5 is cooled by a refrigerator 8. An infrared or far-infrared ray generated in an infrared or far-infrared ray interferometer 9 is irradiated to a superconductor film through a light pipe 6, and the transmitted infrared or far-infrared ray is measured by a detector 1.

Figure 8:
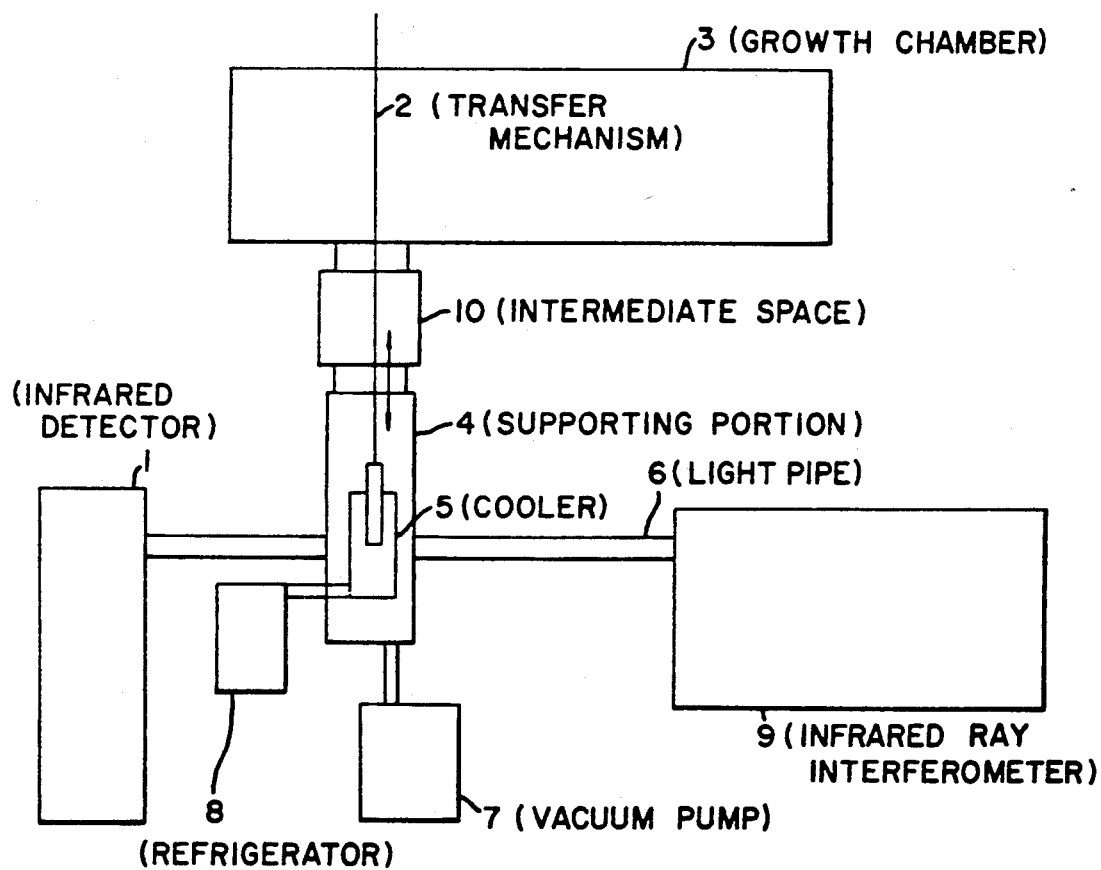
FIG. 8 shows an arrangement of an apparatus for forming superconductor films according to the present invention.

As shown in FIG. 8, an intermediate space 10 is provided between the film growth chamber 3 and the film supporting portion 4. The inside of the intermediate space 10 is maintained at a temperature and a pressure between those of the growth chamber 3 and the supporting portion 4 by a not-shown regulator, to avoid an abrupt thermal change in the transported film and an influence between the atmospheres of the growth chamber 3 and the supporting portion 4.

EXAMPLE 5

A process for forming superconductor films by using the present inventive evaluation method may be carried out in the apparatus as shown in FIG. 8.

Figure 9:
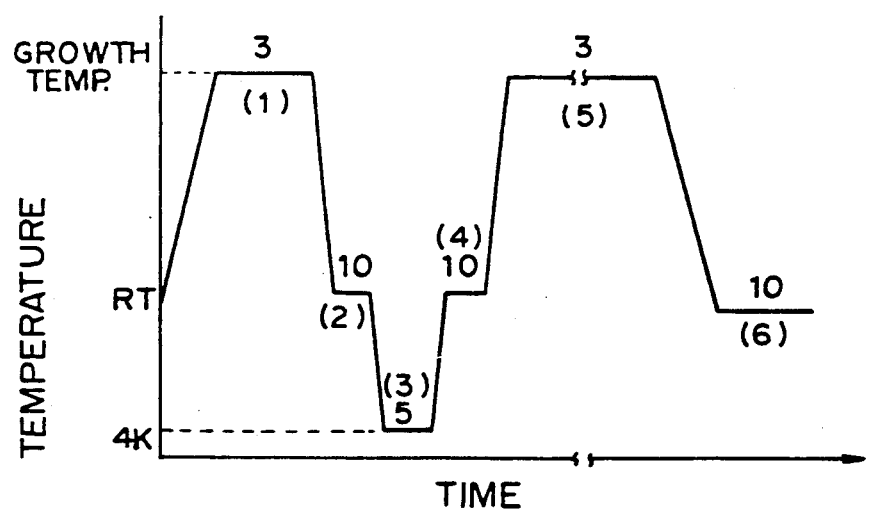
FIG. 9 shows a process sequence according to the present invention.

FIG. 9 shows a process sequence according to the present invention. In FIG. 9, the reference numerals in parentheses [(1) to (6)] represent the process sequence or steps and the numerals without parentheses [3, 5, and 10] correspond to those of the apparatus shown in FIG. 8.

Step (1)

A substrate is placed in the film growth chamber 3 and held at a growth temperature to grow a Bi—Sr—Ca—Cu—O superconductor film on the substrate.

Step (2)

After the film has grown to a certain thickness, the substrate and the film are transferred to the intermediate space 10 and cooled to around room temperature.

Step (3)

The substrate and the film are then transferred to the cooler 5 of a measuring apparatus, to measure the transmission spectrum T by the method according to the present invention. The film is evaluated from the measured transmission spectrum.

Step (4)

The substrate and the film are then transferred to the growth chamber through the intermediate space 10.

Step (5)

In the growth room 3, the film is allowed to grow on the substrate again under a growth condition different from the initial condition of Step (1), if necessary, based on the evaluation obtained at Step (3).

Step (6)

The substrate and the film are transferred to the intermediate space 10 for a further evaluation.

The step cycle (1)–(6) is repeated until the film has been grown to a desired thickness. Namely, the film is taken out of the growth chamber, for an evaluation thereof, at any time during the growth thereof and the evaluation film property is fed back to change the process conditions to thus obtain a controlled film property. This is also applicable when forming of a multilayer film, using the same apparatus as shown in FIG. 8.

The present invention is applicable not only to a film sample but also to a bulk sample which transmits light.

The superconductor must be carefully formed under a precisely controlled condition, because the superconductive property is very dependent upon the chemical composition. The provision of an infrared or far-infrared ray spectrometer in an apparatus for forming superconductor films enables a growing superconductor film to be taken out of a film growth chamber at any desired time, for a measurement of the normal/superconduction electron number ratio, to thus provide a frequent feedback for changing the film formation conditions, to thereby ensure a controlled optimum condition for a desired superconductive property.

As herein described, the present invention provides a method of evaluating a superconductor at a high precision even when a mass to be evaluated is as small as that of a film. The present invention also provides a process and an apparatus for forming superconductor films, in which a superconductor film can be evaluated at any time during the growth or formation process thereof, to obtain a superconductor film having a good crystalline structure and applicable to many purposes including electronic elements.

We claim:

1. A method of evaluating the characteristics of superconductors, comprising:

irradiating light to a superconductor held at a predetermined temperature;

detecting light transmitted through the superconductor and composing a spectrum of the transmitted light; and using the spectrum to calculate a ratio of the number of electrons contributing to a normal conduction to the number of electrons contributing to a superconduction in the superconductor, the ratio being effective at said predetermined temperature.

2. A method according to claim 1, wherein said calculation comprises:

comparing an observed spectrum of the transmitted light with a theoretical spectrum T defined by the following formula (1); and calculating said ratio by using the following formula (2).

$$T = \frac{(1-R)^2 \left(1 + \frac{K^2}{n^2}\right) e^{-\alpha d}}{(1 - Re^{-\alpha d})^2 + 4Re^{-\alpha d} \sin^2(\phi - \theta)} \quad (1)$$

provided $$R = \frac{(n-1)^2 + K^2}{(n+1)^2 + K^2}, \; \alpha = \frac{\omega}{cn} \epsilon_2$$

$$n = (((\epsilon_1^2 + \epsilon_2^2)^{\frac{1}{2}} + \epsilon_1)/2)^{\frac{1}{2}},$$

$$k = (((\epsilon_1^2 + \epsilon_2^2)^{\frac{1}{2}} - \epsilon_1)/2)^{\frac{1}{2}},$$

$$\theta = knd,$$

$$\tan \phi = \frac{-2k}{n^2 + k^2 - 1}$$

where R: reflectance, n: real part of complex refractive index, k: imaginary part of complex refractive index, α: absorption coefficient, d: thickness of sample.

$$\epsilon = \epsilon^\infty + f_n \epsilon_d + (1 - f_n) \epsilon_s \quad (2)$$

where

ε: complex dielectric constant, $\epsilon^\infty$: high frequency term not contributing to conduction;

$\epsilon_d$: term due to normal conduction electrons (or free electron gas), which conforms to Drude's formula and defined as;

$$\epsilon_d = \epsilon_{1d} - i\epsilon_{2d}$$

provided $$\epsilon_{1d} = -\frac{\omega_p^2 \tau^2}{\omega^2 \tau^2 + 1},$$

$$\epsilon_{1d} = -\frac{\omega_p^2 (\tau/\omega)}{\omega^2 \tau^2 + 1},$$

$$\epsilon_p^2 = \frac{N e^2}{\epsilon_0 m^*}$$

where
$\tau$: relaxation time of carrier
$\omega_p$: plasma frequency
N: electron density
$m^*$: effective mass of electron
$\epsilon_s$: term due to superconduction electrons and defined as;

$$\epsilon_s = \epsilon_{1s} - i\epsilon_{2s}$$

where $\epsilon_0 \epsilon_{2s} = \sigma_{1S}/\omega$ and $\epsilon_0 \epsilon_{1s} = -\sigma_{2S}/\omega$, $\sigma_{1S}$ and $\sigma_{2S}$ being the real part and the imaginary part of the optical conductivity spectrum of a superconductor which conforms to Mattis-Bardeen's rule, and
$f_n$: ratio of the number of normal conduction electrons to the total numbers of electrons contributing to conduction.

3. A method according to claim 1, wherein said calculation comprises:
comparing an observed spectrum of the transmitted light with a theoretical spectrum T defined by the following formula (1A); and
calculating said ratio by using the following formula (2).

$$T = T_{0,j} = t_{o,j} t_{o,j}^* \qquad (1A)$$

wherein $$r_{o,j} = r_{o,j-1} + \frac{t_{o,j-1} \cdot t_{j-1,0} \, e^{-2i\Delta_j}}{1 + r_{j-1,0} \cdot r_{j-1,j} \, e^{-2i\Delta_j}}$$

$$t_{o,j} = \frac{t_{o,j-1} \cdot t_{j-1,j} \, e^{-i\Delta_j}}{1 - r_{j-1,0} \cdot r_{j-1,j} \, e^{-2i\Delta_j}}$$

where
$r_{k,l}$ represents the phase and amplitude of light once reflected through the k-th to the l-th layers in a multiple-layered film composed of j layers,
$t_{k,l}$ represents the phase and amplitude of light once transmitted through the k-th to the l-th layers in a multiple-layered film composed of j layers, and
$e^{-\Delta_n}$ represents the phase shift and damping in the material of the n-th layer, in which $\Delta_n = (d_n/\lambda)/2\pi + i \, e^{-\alpha_n d_n}$, $d_n$ being the thickness of the n-th layer and $\alpha_n$ being the damping of the n-th layer, $$\epsilon = \epsilon^\infty + f_n \epsilon_d + (1 - f_n)\epsilon_s \qquad (2)$$

where
$\epsilon$: complex dielectric constant,
$\epsilon^\infty$: high frequency term not contributing to conduction,
$\epsilon_d$: term due to normal conduction electrons (or free electron gas), which conforms to Drude's formula and defined as;

$$\epsilon_d = \epsilon_{1d} - i\epsilon_{2d}$$

provided $$\epsilon_{1d} = -\frac{\omega_p^2 \tau^2}{\omega^2 \tau^2 + 1},$$

$$\epsilon_{1d} = -\frac{\omega_p^2 (\tau/\omega)}{\omega^2 \tau^2 + 1},$$

$$\epsilon_p^2 = \frac{N e^2}{\epsilon_0 m^*}$$

where
$\tau$: relaxation time of carrier
$\omega_p$: plasma frequency
N: electron density
$m^*$: effective mass of electron
$\epsilon_s$: term due to superconduction electrons and defined as;

$$\epsilon_s = \epsilon_{1s} - i\epsilon_{2s}$$

where $\epsilon_0 \epsilon_{2s} = \sigma_{1S}/\omega$ and $\epsilon_0 \epsilon_{1s} = -\sigma_{2S}/\omega$, $\sigma_{1S}$ and $\sigma_{2S}$ being the real part and the imaginary part of the optical conductivity spectrum of a superconductor which conform to Mattis-Bardeen's rule, and
$f_n$: ratio of the number of normal conduction electrons to the total numbers of electrons contributing to conduction.

4. A method according to claim 2 or 3, wherein said real part $\sigma_{1S}$ and said imaginary part $\sigma_{2S}$ of the optical conductivity spectrum of a superconductor conform to Leplae's theory, as defined by the following formule:

$$\sigma_{1s}(\omega, V_F \tau) =$$

$$\frac{1}{2\hbar\omega} \int_\Delta^{\hbar\omega - \Delta} \{[g(E) + 1]\sigma_{1d}(|\epsilon'| + |\epsilon|, V_F \tau) +$$

$$[g(E) - 1]\sigma_{1d}(|\epsilon'| - |\epsilon|, V_F \tau)\}dE$$

$$\sigma_{2s}(\omega, V_F \tau) = \frac{2A(V_F \tau)}{\pi\omega} + \frac{2\omega}{\pi} \int_{0+}^\infty \frac{\sigma_{1s}(\omega', V_F \tau)}{\omega^2 - \omega'^2} d\omega'$$

with
$\epsilon, \epsilon'$: energy of a single particle electron measured from Fermi surface, $\epsilon'$ being the energy under an excited state,
$g(E): (EE' - \Delta^2)/|\epsilon \, \epsilon'|$,
$\Delta$: energy gap,
$\sigma_{1d}: \sigma_0/(1 + \omega^2 \tau^2)$ [derived from Drude's equation], $$A(V_F \tau) = \int_0^\infty \sigma_{1s}(\omega, V_F \tau)d\omega - \int_0^\infty \sigma_{1s}(\omega, V_F \tau)d\omega$$

$\sigma_0$: direct current electric conductivity, and
$V_F$: Fermi velocity.

5. A method according to claim 1, wherein said irradiation is effected with an infrared or far-infrared ray.

6. A process for forming a superconductor film on a substrate, comprising:
   using the method according to claim 1, evaluating characteristics of a superconductor during a growth thereof on a substrate; and
   controlling a process condition based on a result of the evaluation.

7. A process according to claim 6, wherein said forming of the superconductor film on the substrate is carried out by a chemical vapor deposition (CVD), a molecular beam epitaxy (MBE), a sputtering, or a vapor deposition.

8. An apparatus for forming a superconductor film on a substrate, comprising:
   a growth chamber in which a superconductor film is formed on a substrate;
   a means for measuring a light transmittance of a superconductor film on the substrate; and
   a mechanism for transferring the substrate and the film between the growth chamber and the means for measuring a light transmittance.

9. An apparatus according to claim 8, wherein said means for measuring a light transmittance of a superconductor film comprises: a portion for generating light; a portion for detecting light; a light pipe for communicating the light generating portion with the light detecting portion; and a means, inserted in the light pipe, for supporting the substrate with the film in the path of light passing through the light pipe: and wherein said mechanism for transferring the substrate with the film is able to transfer the substrate and the film between the growth chamber and the substrate supporting portion of the means for measuring a light transmittance.

10. An apparatus according to claim 9, wherein an intermediate space is provided between the growth chamber and the substrate supporting means, for temporarily containing the substrate and the film when moved between the growth chamber and the substrate supporting means.

11. An apparatus according to claim 10, which further comprises a temperature regulator and a pressure regulator for maintaining a temperature and a pressure in the intermediate space at a value between those of the growth chamber and those of the substrate supporting means.

12. An apparatus according to claim 9, 10, or 11, wherein said growth chamber is a growth chamber of a chemical vapor deposition apparatus, a molecular beam epitaxy apparatus, a sputtering apparatus, or a vapor deposition apparatus.

* * * * *